United States Patent [19]

Lamparsky et al.

[11] 3,952,062

[45] Apr. 20, 1976

[54] MERCAPTO- OR ALKYLTHIO-SUBSTITUTED MENTHENONES

[75] Inventors: Dietmar Lamparsky, Wangen-Dubendorf; Peter Schudel, Grut, near Wetzikon, both of Switzerland

[73] Assignee: Givaudan Corporation, Clifton, N.J.

[22] Filed: Apr. 26, 1974

[21] Appl. No.: 464,416

Related U.S. Application Data

[62] Division of Ser. No. 69,457, Sept. 3, 1970.

[30] Foreign Application Priority Data

Sept. 10, 1969 Switzerland.................... 13748/69

[52] U.S. Cl............................. 260/586 R; 252/522; 260/586 G; 260/586 F; 260/593 R; 260/598; 260/601 R; 426/534

[51] Int. Cl.²......................................... C07C 49/48

[58] Field of Search................................ 260/586 R

[56] References Cited

UNITED STATES PATENTS

| | | |
|---|---|---|
| 2,465,882 | 3/1949 | Kendall et al.................... 260/586 R |
| 2,586,306 | 2/1952 | Copenhaver..................... 260/586 R |
| 3,723,531 | 3/1973 | Tobias et al..................... 260/586 R |
| 3,820,975 | 6/1974 | Poje................................. 260/586 R |
| 3,845,134 | 10/1974 | Helmluger et al.............. 260/586 R |

*Primary Examiner*—Norman Morgenstern
*Attorney, Agent, or Firm*—Thomas Cifelli, Jr.

[57] ABSTRACT

There are provided novel mercapto- or alkylthio-substituted oxo-terpenoids having 10 carbon atoms in the terpenoid skeleton. These novel compounds may be acyclic monocyclic or bicyclic. The novel compounds are useful as odorants particularly, but also for producing aromas, e.g. of a vegetable note.

3 Claims, No Drawings

MERCAPTO- OR ALKYLTHIO-SUBSTITUTED MENTHENONES

RELATED APPLICATIONS

This is a division of application Ser. No. 69,457 filed Sept. 3, 1970.

This application claims priority from Swiss application 13748/69 filed Sept. 10, 1969.

FIELD OF THE INVENTION

Novel aromatizing agents

SUMMARY OF THE INVENTION

The present invention is concerned with new mercapto- or alkylthio-substituted terpenoids of the general formula

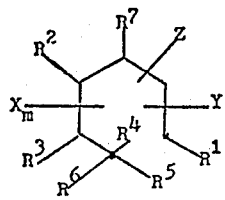

I wherein $R^1$ represents hydrogen or together with $R^4$ represents a C—C bond, $R^2$ represents hydrogen or together with $R^6$ represents a dimethylmethylene group, or, when $R^6$ is isopropyl, together with $R^5$ represents a C—C bond, $R^3$ represents hydrogen or together with $R^6$ represents a dimethylmethylene group, $R^4$ represents hydrogen or together with $R^1$ represents a C—C bond, $R^5$ represents hydrogen or, when $R^6$ signifies isopropyl, together with $R^2$ represents a C—C bond, $R^6$ represents isopropyl or together with $R^2$ or with $R^3$ represents a dimethylmethylene group, $R^7$ represents methyl, X represents a C—C double bond taking the place of a C—C single bond, $m = 0$ to 2, Y represents oxo bound to a primary or secondary C-atom and Z represents mercapto or lower alkylthio located in the $\beta$-position to the carbonyl function, provided that when $R^2$, $R^3$ and $R^5$ represent hydrogen, $R^6$ represents isopropyl, $R^4$ together with $R^1$ represents a C—C bond, Y is $\beta$ to the carbon atom bearing the substituent $R^7$, $m=0$, Z is $\alpha$ to the carbon atom bearing the substituent $R^5$ and $\beta$ to the carbon atom bearing the substituent $R^3$, then Z represents alkylthio, their use as odorants and/or flavourings, as well as a process for their manufacture.

The above formula I includes mercapto- or alkylthio-substituted acyclic, monocyclic or bicyclic monoterpenes each containing a carbonyl group, the mercapto or alkylthio substituent Z being located in the $\beta$-position to the carbonyl function.

DESCRIPTION OF THE PREFERRED EMBODIMENTS

Formula I, as also all other formulae appearing in the description and the claims, is meant to include all stereoisomers.

The above formula I includes the compounds of the following general formulae as sub-groups

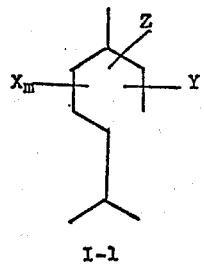

I-1

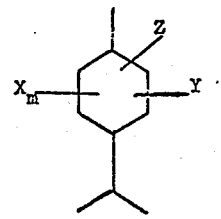

I-2

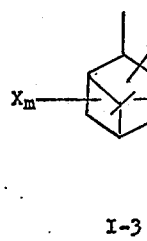

I-3

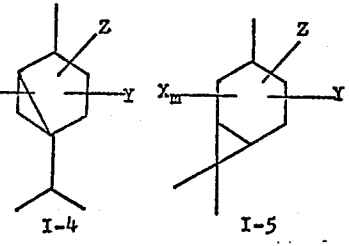

I-4     I-5 the compounds of formulae I-1 and I-2 claiming particular interest.

In formulae I-1 to I-5, X, Y, Z and $m$ have the significance stated above.

The compounds I-1 are acryclic acyclic have a carbon skeleton like, for example, citral or tagetenone. The compounds I-2 are monocyclic and have the p-menthane skeleton. The compounds I-3, I-4 and I-5 are bicyclic and display the skeleton of pinane, thujane or carane.

By lower alkylthio in the sense of the above definition are meant alkylthio residues the alkyl portion of which is straight-chain or branched and preferably contains up to 5 C-atoms; examples of such alkyl residues are: methyl (preferred) ethyl, n-propyl, iso-propyl, n-butyl, sec. butyl, tert. butyl, amyl, etc.

The double bonds represented in the above formula I by X can be located in any position of the molecule, thus, for example, in the ring and/or in the side-chain in cyclic systems. These optionally present double bonds are located between two adjacent C-atoms which are bound to other atoms solely by single bonds.

A primary C-atom in the sense of the above definition is present in the group —CH$_3$, a secondary C-atom in the group —CH$_2$—.

The new terpenoids of general formula I are distinguished by specific aroma and/or odorant properties, especially by berry, spice and vegetable notes, for example in combination with the underlying terpenoids. They can accordingly be used for the aromatisation of foods and delicacies as well as of drinks or as odorants for the manufacture of odorant compositions such as perfumes, or can be used for perfuming technical products, for example, solid and liquid detergents, synthetic washing agents, aerosols or cosmetic products of all kinds (e.g. soaps). These compounds can be used in perfumery because of their intensive green notes. The compounds with Z equal to —SH are distinguished by particularly good tenacity. The odorant compositions utilizing these novel compounds, for example perfumed products, can contain a wide proportional range thereof, from 0.005 to 5.0% by weight may be used.

It is to be understood that the scope of the present invention does not include naturally occurring compounds of general formula I.

The novel compounds of formula I can be used in a wide variety of aromatized products. Because of their berry-like aroma properties, these compounds can be used for producing aroma in foods (e.g. milk drinks, yoghurt, etc.), in delicacies (e.g. confectionery products such as bonbons, soft ice, etc. and in drinks (e.g. mineral waters). They can also be used as aroma enhancers for enhancing the aroma of vegetable, soup and snack food aromas where cabbage-like or onion like aromas are especially desired. Their marked flavourous qualities make use in small concentration possible. A suitable dosage comprises the range of 0.01 ppm to 100 ppm, preferably of 0.1 ppm - 1 ppm, in the finished product.

The new compounds of general formula I can be obtained in accordance with the invention by reacting a compound of the general formula

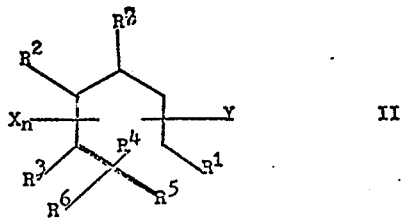

II wherein R to R$^7$, X and Y have the above significance and $n = 1$ to 3, a double bond represented by X being located in the $\alpha,\beta$-position to the carbonyl function or being isomerisable into this position, with a compound HZ (wherein Z signifies the same as above) in the presence of a base under anhydrous conditions, provided that where R$^2$ and R$^3$ are hydrogen, R$^4$ together with R$^1$ represents a C—C-bond, Y is $\beta$ to the carbon atom bearing the substituent R$^7$, R$^5$ where present is hydrogen and R$^6$ is isopropenyl or isopropylidene, $n = 1$, then HZ is a lower alkylmercaptan.

As bases there come into consideration, for example: inorganic bases, for example alkali metal hydroxides such as sodium hydroxide or potassium hydroxide, alkaline earth hydroxides such as, for example, calcium hydroxide, organic bases, for example amines such as alkylamines (e.g. diethylamine or triethylamine), heterocyclic amines such as piperidine etc.

By a double bond isomerisable into the $\alpha,\beta$-position to the carbonyl function is meant that double bond in the molecule which is capable under the influence of bases at elevated temperature of migrating into the desired $\alpha,\beta$-position from another position (e.g. $\beta,\gamma$-position).

The reaction of the starting compounds of general formula II in the presence of the said bases is expediently effected in the presence of a solvent. Suitable solvents are, for example, alcohols such as alkanols (e.g. methanol, ethanol, isopropanol, ethanol being preferred), or ethers such as diethyl ether (preferred), or diisopropyl ether.

However, if desired one can also work in the absence of a solvent, especially when the starting material of formula II is brought to reaction with a lower alkylmercaptan. The reaction temperature expediently lies between about 0°C and 100°C; a range between about 40° and 60°C is preferred. The duration of the reaction depends on the reaction temperature. For example it amounts to about two hours for a reaction temperature of 40° to 60°C.

The reaction of the present invention can also be initiated by the provision of a free radical initiator, suitably ascaridol or $\alpha,\alpha'$-azo bis isobutyronitrile.

The reaction can be carried out at normal pressure or expediently at elevated pressure (e.g. 10 atm.), since the reaction proceeds with reduction in volume.

The proportion of the starting compound of general formula II to the sulphur compound HZ can be varied within wide limits; preferably, at least 1 mol of sulphur compound HZ is used per mol of starting compound II. The sulphur compound HZ can, however, also be used in excess.

The reaction of the starting compound II with the sulphur compound HZ is expediently initiated by treating the starting compound II or the solution of this starting compound in an anhydrous solvent with the sulphur compound HZ in the presence of a base (which can be added as such or dissolved in one of the above-named solvents) at a temperature below the boiling point of the sulphur compound HZ and heating the mixture to the reaction temperature in a suitable pressure vessel.

New asymmetric centres can result by the reaction of the starting compound II with the sulphur compound HZ, and consequently the reaction product can be obtained in the stereoisomeric forms thereby possible.

The reaction product can be isolated from the reaction mixture according to conventional methods; for example, by distilling off the solvent, if necessary, filtration of elementary sulphur which was formed from the residual mixture and fractional distillation, by which means the product can be separated from unreacted starting compound II.

In the following Examples the temperatures are stated in degrees centigrade.

EXAMPLE 1

15.2 g of piperitone are dissolved in 30 ml of absolute ether and treated with 1.0 g triethylamine. The solution is cooled to ca −75°. At this temperature, a total of 5 ml of hydrogen sulphide is condensed in in the course of an hour, the solution initially colouring yellow and later depositing a red-yellow precipitate. After completed $H_2S$—condensation, the reaction product is rapidly transferred into an autoclave, rinsed with 50 ml of absolute ether and allowed to stand for 29 hours. The pressure rise during the gradual heating to room temperature is very slight, so that a pressure-resistance of the apparatus of 10 atm. is sufficient. The solution is thereupon filtered and concentrated. The residue (16.9 g) is fractionally distilled in vacuum. After removal of 7.8 g of unreacted piperitone there are thus obtained 1.6 g of p-menthane-1-thiol-3-one of boiling point 57°–59°/0.05 mm Hg, $n_D^{20}$ 1.4932, in the form of two stereoisomers in the ratio 1:4. (The cis-p-methane-1-thiol- 3-one can be separated from the trans-p-menthane-1-thiol-3-one gas-chromatographically).
Odour of the product: sulphurous, minty, reminiscent of rhubarb, but also suitable for cassis and blackberry notes.

EXAMPLE 2

15 g of carvone are treated with a solution of 1 g of KOH in 100 ml of absolute ethanol. $H_2S$ is condensed into the solution, cooled to −75°, until ca 20 ml of $H_2S$ are condensed. After standing overnight in an autoclave at room temperature, the mixture is heated to 50° for 2 hours (in so doing, the pressure rises to 8.5 atm.), then cooled, taken up in ether, the ethereal solution washed with saturated NaCl solution, dried and concentrated. The residue (14.3 g) is fractionally distilled in vacuum. The distillate (6.3 g) of boiling point 77°–78°, $n_D^{20}$ 1.5248 to 1.5229, contains, besides ca 10% of unreacted starting material, a mixture of stereoisomeric p-menth-8-ene-6-thiol-2-ones in the ratio of ca 1:1:1.
Odour: Green with sulphurous note, reminiscent of thyme and roast onions.

EXAMPLE 3

15.2 g of citral (mixture of geranial and neral) are dissolved in 50 ml of absolute ether and treated with 1 g of triethylamine. The mixture is cooled to −70° and 10 ml of hydrogen sulphide are condensed in. After decanting into a pressure vessel, the reaction mixture is allowed to stand overnight at room temperature and then it is heated to 50° for 2 hours. After cooling and removal of the ether, in the residue, only a little citral can still be detected besides the reaction product obtained.
Odour: intensive, long-lasting, reminiscent of rhubarb.

EXAMPLE 4

15.2 g of pulegone are treated with 0.5 ml of triethylamine and cooled to ca 0° by means of an ice-common salt mixture. With stirring, methyl mercaptan in excess is condensed into the mixture and, after condensation of 200% of the calculated amount, the mixture is transferred into an autoclave. After standing overnight at room temperature, the reaction mixture is heated to 50° and, after cooling of the autoclave, the reaction product immediately distilled in vacuum. 9.8 g of 8-methylthio-p-menthan-3-one are obtained as a clear liquid with pleasant odour reminiscent of peppermint, geranium and caraway, boiling point 72°–73°/0.15 mm Hg, $n_D^{20}$ 1.4982. The yield amounts to 73% of the theory based on reacted pulegone. The two stereoisomeric compounds 8-methylthio-cis-p-menthan-3-one and 8-methylthio-trans-p-menthan-3-one obtained can be separated gas-chromatographically.

EXAMPLE 5

15.2 g of piperitone and 0.5 g of triethylamine are cooled to −5°. 15 ml of methyl mercaptan are condensed in with stirring. The mixture is treated and worked up as in Example 4. By fractional distillation, unreacted piperitone is distilled off from the reaction mixture, and the 1-methylthio-p-menthan-3-one enriched to 95% content (boiling point 88°/0.1 mm Hg, $n_D^{20}$ 1.4990). The yield amounts to 6.2 g or 48% of the theory, based on reacted piperitone. The odour of the product is reminiscent of dill and caraway as well as of boiled white cabbage.

EXAMPLE 6

15.0 g of carvone are mixed with 0.5 g of triethylamine. 20 ml of methyl mercaptan are condensed in this mixture at room temperature. After standing overnight in the autoclave, the mixture is heated to 50°C for a further 2 hours. After removal of the excess methyl mercaptan, the reaction product is fractionally distilled in vacuum. After a small fore-run of unreacted carvone, there are obtained 14.9 g of 6-methylthio-p-menth-8-en-2-one in the form of a mixture of two isomers in the ratio 1:4 (boiling point 105°–107°10.2 mm Hg, $n_D^{20}$ 1.5067), corresponding to a yield of 78% of the theory. The odour of the mixture is reminiscent of boiled white cabbage with a caraway and onion peel note.

EXAMPLE 7

15. g of citral and 0.5 of triethylamine are treated with methyl mercaptan as described in Example 6. After removal of the excess point methyl mercaptane, there is obtained a practically citral-free crude product (16 g) which after distillation yields, besides a polymeric residue, 10.4 g of 3,7-dimethyl-3-methylthio-6-octenal, corresponding to a yield of 52% of the theory (boiling poin 82°–84°/0.2 mm Hg, $n_D^{20}$ 1.4961). The odour of the compound is reminiscent of kohlrabi and cauliflower with a slight citral note.

EXAMPLE 8

Into a suitable autoclave there are charged 9.0 g of 3-caren-2-one, 0.3 g of triethylamine and 4 drops of ascaridol. The autoclave is cooled to −20° and 10 ml of methylmercaptan distilled thereinto. The autoclave is sealed permitted to stand overnight at room temperature and subsequently warmed to 50°C for 2 hours. The reaction mixture is fractionally distilled to yield 4-methylthio-2-carone (2.8 g) in the form of 2 stereoisomers having a boiling point of 80°–85°C at 0.1 mm, $n_D^{20}$ 1.5210.
The odor of the compound is green and earthy. The resulting aroma is vegetable like and is also reminiscent of the aroma of the tonka bean.

EXAMPLE 9

In accordance with the procedure of Example 7 verbenol is reacted with methylmercaptan to yield 1-methylthioverbanone, boiling point 70° at 0.1 mm Hg, $n_D^{20}$ = 1.5080 (product of 70% purity).

EXAMPLE 10

In accordance with the procedure of example 7 myrtanal is reacted with methylmercaptan to yield 2-methylthio-myrtanal, boiling point 76° at 0.3 mm Hg, $n_D^{20}$ = 1.5170. This product contains as an impurity 10% of a by-product. The aroma of the product is leek-like and is reminiscent of cabbages and onions. The undertone is woody and green.

EXAMPLE 11

In accordance with the procedure of Example 8 car-3-en-5-one is reacted with methylmercaptan by heating the reaction mixture in a suitable pressure-vessel for 3 hours to yield 3-methylthio-caran-5-on, boiling point ca 70° at 0.5 mm Hg, $n_D^{20}$ = 1.5224.

The odor of the compound is reminiscent of garlic and shallots and has a fainter smell of rhubarb and vegetables. As side notes of the aroma the aroma of balsam, spices and smoke can also be smelt.

EXAMPLE 12

Odorant Composition Having a Lavender Note

Parts by Weight:

| | |
|---|---|
| 50 | 6-Mercapto-p-menth-8-en-2-one 10% (in PDE) |
| 100 | Spanish Wood Oil |
| 450 | Lavender Oil Mont Blanc |
| 200 | Linalyl acetate |
| 50 | Linalool |
| 50 | p-tert-Butyl-cyclohexyl-acetate |
| 5 | Coumarin |
| 25 | Cinnamyl alcohol synth. |
| 5 | Undecylenaldehyde 10% (in PDE) |
| 25 | Terpineol |
| 85 | Benzyl alcohol |
| 5 | 1,1,4,4-Tetramethyl-6-ethyl-7-acetyl-1,2,3,4-tetrahydronaphthalene |
| 1050 | |

PDE = diethylphthalate

The added 6-mercapto-p-menth-8-en-2-one enhanced the diffusion and strengthened the floral impression of the composition.

EXAMPLE 13

Eau de Cologne Composition

Parts by Weight:

| | |
|---|---|
| 25 | 6-Mercapto-p-menth-8-en-2-one 10% (in PDE) |
| 400 | Bergamotte oil Reggio |
| 200 | Italian Lemon oil |
| 200 | Californian Orange oil |
| 35 | Neroli oil synth. |
| 5 | Peppermint oil italo-Mitch. rect. |
| 25 | Lavender oil Mont Blanc |
| 10 | Methylnaphthylketone cryst. |
| 50 | Linalyl acetate |
| 20 | Citral B pure |
| 10 | $C_{10}$-Aldehyde 10% (in PDE) |
| 10 | 1,1,4,4-Tetramethyl-6-ethyl-7-acetyl-1,2,3,4-tetrahydronaphthalene |
| 5 | p-tert-Butyl-alpha-methylhydrocinnamaldehyde |
| 30 | Nerolidol |
| 1025 | |

The 6-mercapto-p-menth-8-en-2-one added as a solution of its crystalline adduct considerably enhanced the diffusion and rounded the bouquet off.

EXAMPLE 14

Aromatisation of a powdered soup

A neutral testing powdered soup preparation was prepared according to the following recipee.

| | |
|---|---|
| 18% | NaCl |
| 12% | Sugar |
| 10% | Sodium glutamate |
| 10% | hydrolyzed vegetable proteins |
| 50% | corn starch |
| 100% | |

For the preparation of 1 liter neutral-testing soup 45 g of this preparation are necessary. The addition of 2,7–3,5g 6-methylthio-p-menth-8-en-2-one per 100 l of soup imparted to the neutral-testing soup a pleasant onion and leek-taste.

EXAMPLE 15

Aromatisation of mashed potatoes

Neutral testing mashed potatoes are prepared by mixing of
15 g potato flakes and
85 g water.

The addition of 3–4 g of 6-methylthio-p-menth-8-en-2-one per 100 kg of mashed potatoes imparted to the product a leek-taste; the thiolone (1,5–2 g) in 0,5% NaCl (100 l $H_2O$) imparted to such solution a predominant note of horseraddish and onion.

What is claimed is:

1. p-Menthane-1-thiol-3-one.

2. 8-Methylthio-p-menthan-3-one.

3. 1-Methylthio-p-menthan-3-one.

\* \* \* \* \*